United States Patent [19]

Murphy

[11] 4,286,639
[45] Sep. 1, 1981

[54] THIN WALLET CARRYING CASE FOR A SANITARY NAPKIN OR TAMPON

[76] Inventor: Jeannie P. Murphy, 2330 Good Hope Rd. SE., Apt. 904, Washington, D.C. 20020

[21] Appl. No.: 145,106

[22] Filed: Apr. 30, 1980

[51] Int. Cl.³ .................... B65D 30/24; B65D 39/00
[52] U.S. Cl. ............................ 150/7; 150/42; 206/440
[58] Field of Search ............ 150/7, 42, 52 R; 206/440, 438

[56] References Cited

U.S. PATENT DOCUMENTS

| | | | |
|---|---|---|---|
| 1,659,185 | 2/1928 | Baker | 150/7 X |
| 3,557,853 | 1/1971 | Jones | 150/7 |

*Primary Examiner*—George T. Hall
*Attorney, Agent, or Firm*—Abraham A. Saffitz

[57] ABSTRACT

A generally rectangular flexible flat wallet-like carrying case produced from a single sheet comprising an adjacent single sheet thickness front and back panel formed by folding one end of said single sheet over and adjacent a portion of the remainder of said single sheet, said panels secured together at opposing side edges and open at the top to form a single pocket between said front and back panels, said back panel being folded adjacent to the open pocket so as to lie flat on top of the front panel to form a long, flexible closure flap with respect to the width of the carrying case, releasable fastening means extending beyond and overlying the mid-portion of the pocket for securing said closure flap in the closed position, and a plastic liner within said pocket, so that upon releasing the fastening means will facilitate insertion or withdrawal of a tampon or sanitary napkin held between the front and back panels in flat condition, preventing attention being directly called to the opening and closing operation as part of the use to which said tampon or sanitary napkin is to be put.

7 Claims, 12 Drawing Figures

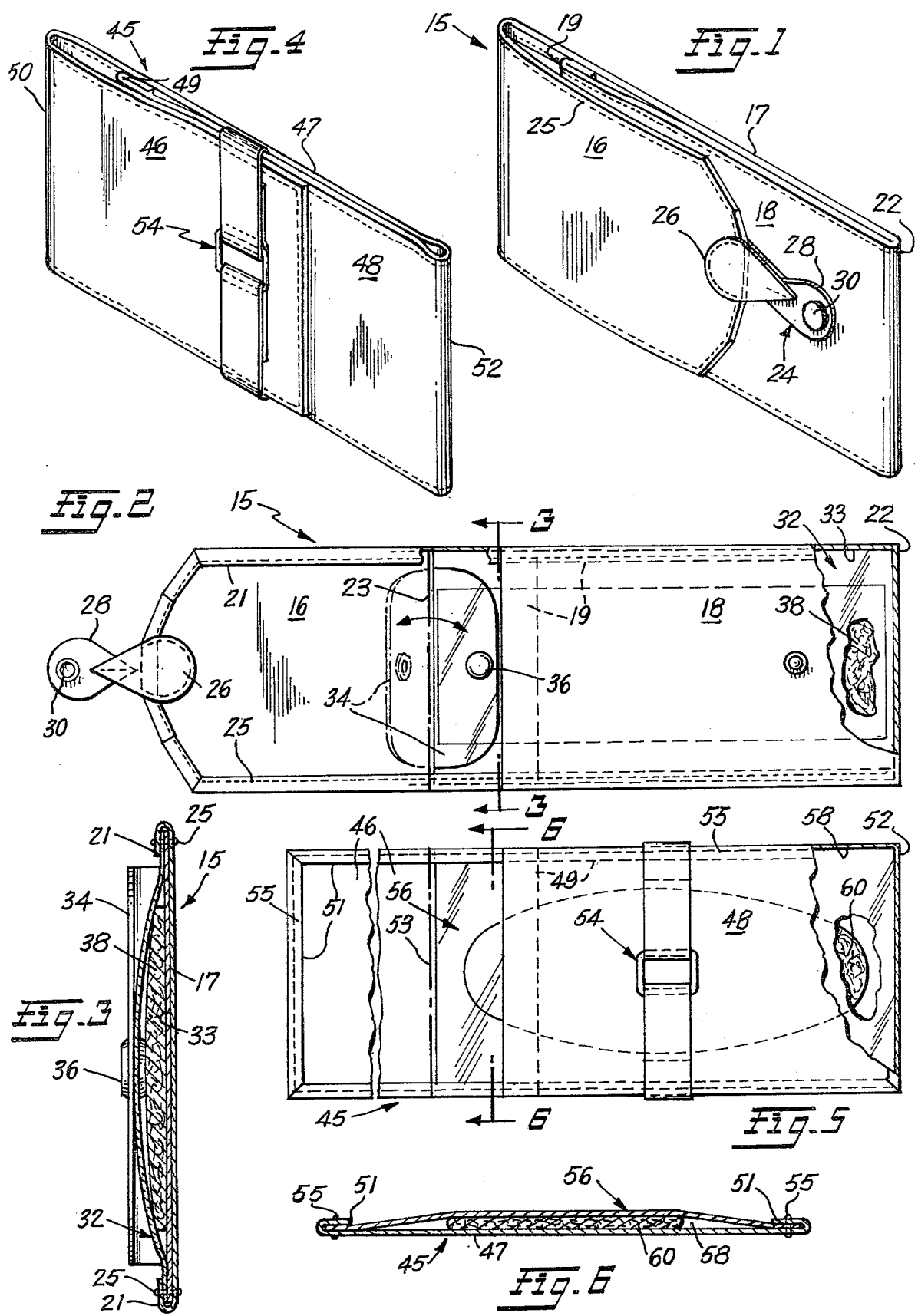

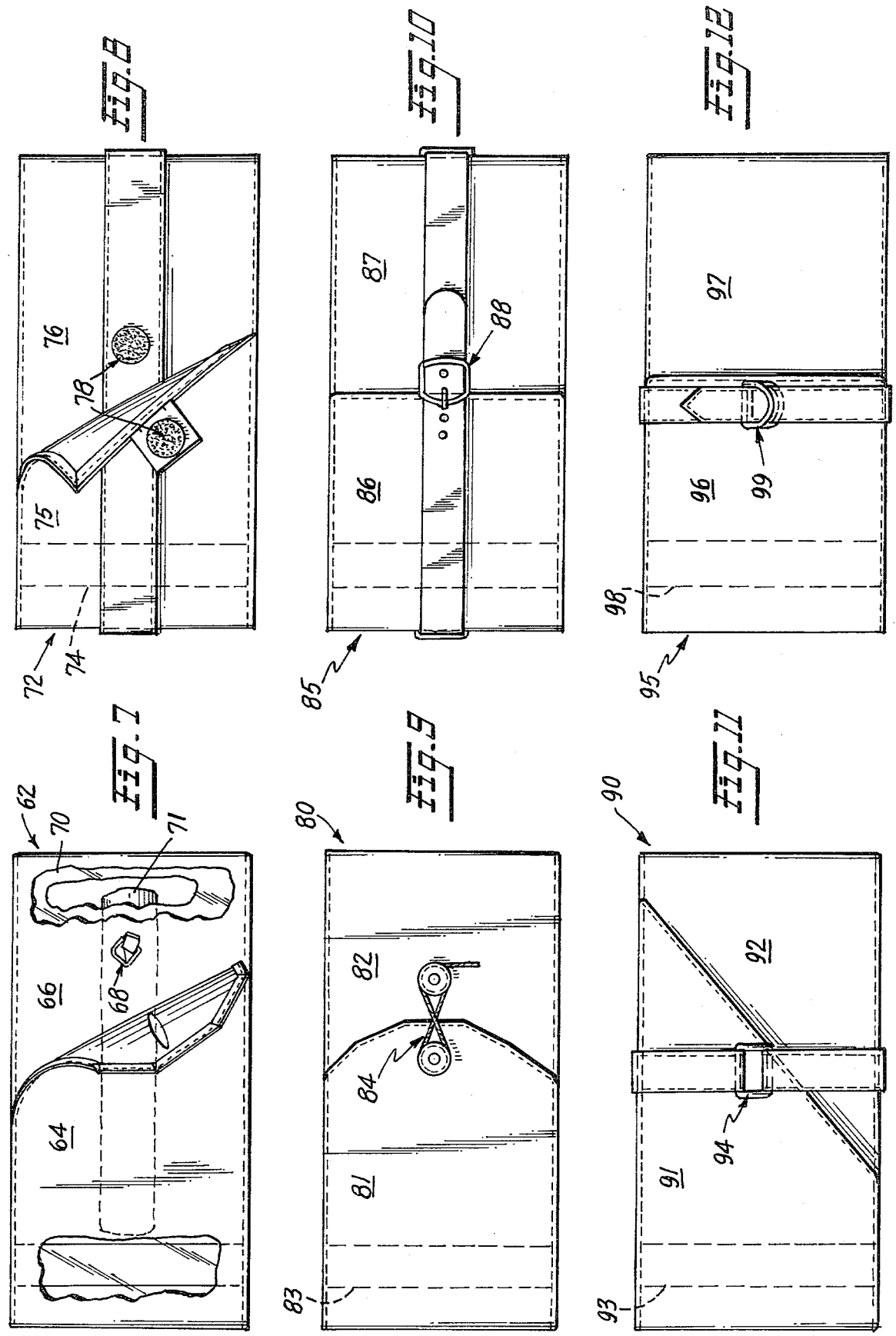

THIN WALLET CARRYING CASE FOR A SANITARY NAPKIN OR TAMPON

BACKGROUND OF THE INVENTION

1. Field of the Invention

This invention lies in the general field of cloth, leather and rubber flexible receptacles or carrying cases. In this instance, a generally rectangular flat wallet-like thin flexible carrying case comprising a closure flap portion is adapted to open and close a pocket in the body of the case concealing a tampon or sanitary napkin which may be easily inserted or withdrawn from the pocket.

2. Brief Description of the Prior Art

The basic concept of a carrying case for sanitary napkins is shown in FIG. 4 of the patent to Frankfurt, U.S. Pat. No. 2,843,170. This patent shows a carrying case for sanitary napkins of the above type wherein a pair of sanitary napkins are inserted and are completely enclosed by a double closure compartment, one for the napkins and a further compartment for miscellaneous articles.

While the above mentioned patent discloses the same general purpose, the construction of the case is entirely different, due to its double compartments. It is very bulky and cumbersome and it requires the opening or closing of two separate closure flaps. Thus, the patent does not teach the concept of a thin flat wallet-like carrying case having a single pocket for discretely concealing a tampon or sanitary napkin within the pocket of the case.

Another teaching of a carrying case is shown in the patent to May, U.S. Pat. No. 1,429,608. In FIG. 1 of this patent, there is shown a traveler's case comprising a stiff base wherein a resilient stack of cloth articles may rest, combined with a band secured to said base.

A further teaching of a carrying case is shown in the patent to March, U.S. Pat. No. 1,672,766. In FIG. 1 of this patent, there is shown a leather case formed with a plurality of tapered pockets for gripping cigars.

In neither of the patents to May nor March is there a teaching of the basic concept of a rectangular, flat, flexible wallet-like carrying case provided with a single pocket and a plastic liner therein wherein a sanitary napkin or tampon are easily inserted and enclosed by a single closure flap.

OBJECTS OF THE INVENTION

An object of the invention is to provide a flexible flat wallet-like carrying case for a tampon or sanitary napkin.

A further object of the invention is to provide a carrying case for tampons or sanitary napkins which is provided with a plastic liner within a pocket of the case which is substantially air tight, dust free and impervious to water.

It is another object of the present invention to provide a carrying case for catamenial devices of the above type which is rectangularly shaped, small, compact, thin and light in weight and which resembles in size and weight a small wallet.

It is still another object of the invention to provide a flexible and pliable carrying case with a single pocket and a single closure flap sufficiently stiff for preventing the contents while being stored therein from being bent, and releasable fastening means for said flap to facilitate insertion or withdrawal of an article from a pocket formed in said case.

Other objects of the invention are to provide a thin, flat wallet-like container for tampons or sanitary napkins bearing the above objects in mind which is of simple construction, is inexpensive to manufacture, has a minimum number of parts, has a very pleasing and attractive appearance, and is effective and efficient in use.

For other and further objects and for a better understanding of the present invention, reference may be had to the following detailed description taken in connection with the accompanying drawings.

SUMMARY OF THE INVENTION

The invention relates to improvements in flexible carrying cases for a tampon or sanitary napkin. More particularly, the present invention provides a thin, rectangularly shaped carrying case provided with a single pocket open at one end and having a water impervious lining therein, a single closure flap with releasable fastening means extending beyond and overlying the midportion of the pocket for securing said closure flap in closed position, whereby opening the flap will facilitate insertion or withdrawal of a tampon or sanitary napkin held in the pocket.

BRIEF DESCRIPTION OF THE DRAWINGS

FIG. 1 is an isometric view of a preferred embodiment of the present invention of a protective case for a sanitary pad or tampon according to the present invention;

FIG. 2 is a plan view of the case of FIG. 1 shown in its open position and partly in section;

FIG. 3 is an enlarged vertical sectional view, through the open case of FIG. 2, taken on the line 3—3 thereof;

FIG. 4 is an isometric view, similar to FIG. 1, but showing a modification of the case;

FIG. 5 is a fragmentary plan view of the case illustrated in FIG. 4, shown partly in section, and in its open position;

FIG. 6 is an enlarged transverse sectional view, through the open case of FIG. 5, taken on the line 6—6 thereof; and FIGS. 7 through 12 show modification of the closures for the protective case.

DESCRIPTION OF THE PREFERRED EMBODIMENTS

Referring now more in detail to the drawings, a preferred embodiment is illustrated in FIGS. 1 to 3. The protective carrying case 15 represents an elongated rectangular thin flat wallet-like container. The entire carrying case 15 may be constructed of flexible or pliable material, for example, leather, plastic or fabric or other material having suitable physical properties. The protective carrying case 15 is produced from a single sheet of material comprising an adjacent single sheet thickness of a front panel 18 and a back panel 17 formed by folding one end 22 of said single sheet over and adjacent a portion of the remainder of said single sheet forming two layers secured in flat contiguous relation at opposing side edges and open at the top to form a single pocket 33 between said front and back panels, said back panel 17 being folded at 20 adjacent to the open pocket 33 so as to lie flat on top of the front panel 18 to form a long flexible closure flap 16 with respect to the width of the carrying case (FIG. 1). A hem 21 is formed on closure flap 16 by stitching 25 (FIG. 2). An additional hem 19 is formed on front panel 18 over back panel 17, said panels being secured together at opposing side edges by stitching 25. An additional hem 19 is formed on front panel 18. A flap 34 adjacent to the inside fold line 23 is secured by a male snap fastener 36 which mates with a female fastener 37.

As shown in FIGS. 2 and 3, a transparent, low friction, impervious, pliable, plastic envelope or liner 32 of about twenty thousands of an inch thick is secured at its edges to the inner side of pocket 33 to define an inner receptacle 32 open at the top portion into which a tampon or sanitary napkin 38 is placed, the height of said receptacle being sufficient to enclose said tampon or napkin in unfolded condition with a close fit of the closure flap 16 over pocket 33, and preventing it from being bent while being stored therein. Liner 32 may be constructed of suitable plastic materials, such as, Mylar, cellophane or polyester or other substance having physical properties to provide low friction, facilitating the sliding and withdrawal or insertion of the tampon while protecting the tampon against contamination by moisture, dust or the like.

A tab 26 is secured at the edge of closure flap 16 and an additional tab 28 is secured by stitching 27 to tab 28. Tab 28 is provided with a female snap fastener 30 to mate with a male snap fastener 31 on front panel 18. As shown in FIG. 1, the closure flap 16 extends well beyond the mid-portion of front panel 18 and lies flat in contiguous relation thereof to form a thin wallet-like container which provides for insertion and withdrawal of a tampon or sanitary napkin held between front 18 and back 17 panels.

Since the protective carrying case 15 is intended to be carried in a lady's handbag, it is neat and unobtrusive in appearance, and yet provides a sanitary, dust proof, sterile, substantially waterproof and air-tight compartment for carrying a tampon or sanitary napkin, which may be partially opened, as shown in FIG. 2, without disclosing the contents thereof.

A modified case 45 is illustrated in FIGS. 4, 5 and 6 wherein the carrying case is constructed similarly to the above-mentioned case. A closure flap 46, folded at 50 extends well beyond the mid-portion of front panel 48 and back panel 47. A hem 49 is also provided on front panel 48 and an additional hem 51 is provided on closure flap 46, which are secured by stitching 55 (FIG. 5). Fold lines are provided at 52 and 53, respectively (FIG. 5). A modified releasable fastener 54 is provided on strap 57 to secure the closure flap 46 in flat condition against front panel 49 (FIG. 4).

A suitable transparent plastic liner 56 is again inserted and secured in pocket 58 to conceal and carry a tampon or sanitary pad 60, as shown in FIG. 5.

In another modification, case 62 illustrated in FIG. 7, closure flap 64 is contiguous with front panel 66 and is provided with a button-hole 67 for receiving a button fastener 68. A suitable transparent plastic liner 70 is again inserted in the pocket for protection of a tampon or sanitary pad 71.

In another modification, case 72 illustrated in FIG. 8, closure flap 75 is contiguous with front panel 76 and is provided with a VELCRO fastener 78 to mate with a VELCRO strip on front panel 76. Again, a suitable transparent plastic liner 74 is inserted in the pocket.

In yet another modification illustrated in FIG. 9, carrying case 80 is provided with a closure flap 81 in contiguous relation with front panel 82, and is provided with a string fastener 84 provided with buttons 79.

Again, a plastic liner 83 is secured in the pocket to form an inner receptacle.

In still another modification illustrated in FIG. 10, carrying case 85 is provided with a closure flap 86 in contiguous relation with front panel 87, and is provided with a buckle 88 and strap 89.

In yet another modification illustrated in FIG. 11, carrying case 90 is provided with a closure flap 91 in contiguous relation with front panel 92, and is provided with a square shaped keeper 94 on strap 89'. A suitable plastic liner 93 is inserted in the pocket.

In another modification illustrated in FIG. 12, carrying case 95 is provided with a closure flap 96 in contiguous relation with front panel 97, and is provided with D-shaped keepers 99 on strap 89".

Thus, it is clear that in each of the above physical embodiments, a very slim or thin attractive wallet-like flexible carrying case is provided for storing a tampon or sanitary napkin in a sanitary and air-tight manner within an inner plastic liner to define an inner receptacle, wherein the case is light in weight, compact and resembles in external appearance an ordinary wallet which may be discretely opened without disclosing the contents thereof.

I claim:

1. A generally elongated rectangular flexible flat wallet-like carrying case produced from a single sheet comprising:
   (a) an adjacent single sheet thickness front and back panel formed by folding one end of said single sheet over and adjacent a portion of the remainder of said single sheet, forming two layers in flat contiguous relation,
   (b) means securing said panels together at opposing side edges and open at the top to form a single pocket between said front and back panels,
   (c) said back panel being folded adjacent to the open pocket so as to be flat on top of the front panel to define a long flexible closure flap with respect to the width of the carrying case,
   (d) releasable fastening means extending beyond and overlying the mid-portion of the pocket for securing said closure flap in closed position,
   (e) said open pocket under said closure flap providing means for insertion and withdrawal of a tampon or sanitary napkin held between and by the layers formed by the front and back panels in flat condition, preventing attention being directly called to opening and closing operation of the closure flap as part of the use to which said tampon or sanitary napkin is to be put.

2. A generally rectangular flexible flat wallet-like carrying case as claimed in claim 1 wherein a waterproof, low friction impervious plastic lining is secured at its edges to the inner side of said open pocket to define an inner receptacle open at the top into which a tampon is placed, the height of said receptacle being sufficient to enclose said tampon or napkin in unfolded condition with a close fit of said closure flap over said pocket, and said low friction lining facilitating the sliding withdrawal or insertion of said tampon while protecting said tampon or napkin against contamination by moisture, dust or the like.

3. A generally elongated rectangular flexible flat wallet-like carrying case as claimed in claim 1 wherein said releasable fastening means comprises a tab secured to said closure flap provided with a snap fastener adapted to mate with a snap fastener on said front panel.

4. A generally elongated rectangular flexible flat wallet-like carrying case as claimed in claim 1 wherein said releasable fastening means comprises a strap and keeper secured to said closure flap.

5. A generally elongated rectangular flexible flat wallet-like carrying case as claimed in claim 1 wherein said releasable fastening means comprises a button hole on said closure flap adapted to be releasably fastened to a button on said front panel.

6. A generally elongated rectangular flexible flat wallet-like carrying case as claimed in claim 1 wherein said releasable fastening means comprises a VELCRO fastener on said closure flap adapted to be releasably fastened to a VELCRO strip on said front panel.

7. A generally elongated rectangular flexible flat wallet-like carrying case as claimed in claim 1 wherein said releasable fastening means comprises a button on said closure flap and front panel, respectively, said buttons adapted to be secured by a string.

* * * * *